United States Patent [19]

Sasabe et al.

[11] Patent Number: 4,830,727
[45] Date of Patent: May 16, 1989

[54] COMPOSITE PROBE FOR MEASURING THE CONCENTRATION OF AN IMPURITY ELEMENT IN MOLTEN IRON

[75] Inventors: Minoru Sasabe, Chiba; Nobuo Hamada; Toshio Nagatsuka, both of Ichikawa, all of Japan

[73] Assignee: Osaka Sanso Kogyo Ltd., Osaka, Japan

[21] Appl. No.: 194,592

[22] Filed: May 16, 1988

[30] Foreign Application Priority Data

May 19, 1987 [JP] Japan .................. 62-122341

[51] Int. Cl.$^4$ .......................... G01N 27/58
[52] U.S. Cl. ...................... 204/412; 204/422; 436/145
[58] Field of Search ............ 436/145; 204/422, 423, 204/412, 1 T

[56] References Cited

U.S. PATENT DOCUMENTS

| | | | |
|---|---|---|---|
| 3,267,732 | 8/1966 | Hance | 73/359 |
| 3,574,598 | 4/1971 | Kern et al. | 75/60 |
| 4,451,350 | 5/1984 | Tsuchida et al. | 204/422 |
| 4,568,445 | 2/1986 | Cates et al. | 204/415 |

FOREIGN PATENT DOCUMENTS 142455 6/1986 Japan .

OTHER PUBLICATIONS

A New Dynamic Control System at No. 3 BOF in Fukuyama Works Sep. 2–4, 1978, Toronto, Canada, S. Miyoshi et al, 19 pages.

D. E. Krause, "Rapid Test for Carbon Equivalent", *Foundry*, May 1962, pp. 219–218.

*Primary Examiner*—G. L. Kaplan
*Attorney, Agent, or Firm*—R. Hain Swope; Larry R. Cassett

[57] ABSTRACT

A probe for measuring the concentration of an impurity in molten iron is disclosed. The probe comprises three sensors. The first sensor measures the activity of the impurity element directly. The second sensor measures the activity of free oxygen. The third sensor measures carbon content. These values are used are used to give a compensated measure of the impurity element.

1 Claim, 5 Drawing Sheets

COMPOSITE PROBE FOR MEASURING THE CONCENTRATION OF AN IMPURITY ELEMENT IN MOLTEN IRON

BACKGROUND OF THE INVENTION

1. Prior Art

Modern steel products are diverse and are required to meet increasingly stringent quality standards. Under these circumstances, the control of impurity elements in steel products is an important task in the steel industry. In almost all instances, this has been done by sampling a portion of the molten steel to be analyzed and measuring the concentrations of impurity elements in the melt with analytical instruments. However, this method lacks rapidity required in commercial operations.

A method for measuring the concentrations of impurity elements in molten iron with rapidity has recently been proposed (see Japanese Kokai No. 142455/1986). This method uses a probe comprising a solid electrolyte having on its surface a coating layer comprising an oxide of an impurity element to be analyzed or a composite thereof with another oxide. The probe is immersed in molten iron and the oxygen partial pressure created by the reacting of equilibrium between the impurity element of interest and an oxide thereof is measured using the principle of an oxygen concentration electrochemical cell. The probe designed to determine the concentration of an impurity element of interest by this method is hereunder referred to as a chemical potential sensor.

2. Problems of the Prior Art

The sensor described in Japanese Kokai No. 142455/1986 is essentially a chemical sensor utilizing the reaction of chemical equilibrium between impurity elements in molten iron and oxygen at high temperatures. Thermodynamically, no ideal reaction should occur in such a way that only the element to be analyzed will interact with oxygen without being affected by other elements. According to repeated experimentation by the present inventors, measurements of the Si concentration of molten iron are affected by other high-content elements such as C, Al and Ti or those elements which have greater affinity for oxygen. It has therefore become clear that in order to eliminate these defects, some compensation is imperative.

This is technologically a serious problem to the chemical potential sensor under consideration. In the prior art, correct estimation of the concentration of a particular impurity element has been difficult unless the effects of unwanted elements are compensated for by comparison against calibration curves or the concentrations of such elements are already known by measurements with other analytical instruments. In the former case, much data is necessary to construct the calibration curves and the values estimated with the sensor are not reliable if they are outside the applicable range of the calibration curves. In the latter case, the need to use special analytical instruments slows down the analytical procedure. Furthermore, such analytical instruments themselves are capable of determining the concentration of the impurity element and render the use of the sensor meaningless.

The probe of the present invention solves all of the problems described above. It basically consists of two or three sensors, the first sensor comprising a solid electrolyte having oxygen ion conductivity and which has formed on it a coating layer that will provide a constant value of the activity ($a_{M1}$) of an oxide of an impurity element ($M_1$) to be measured in molten iron, and the second and third sensors being designed for measuring the activity of free oxygen ($a_o$) and the content of carbon, respectively. This probe system not only improves the precision of measurements significantly but also expands the range of applicable conditions for measurement.

The present invention provides a composite probe for direct measurement of the concentration of a particular impurity element in molten iron. The probe consists of:

at least one first sensor for measuring the concentration, NM, of an impurity element M in molten iron, said first sensor being composed of a solid electrolyte having oxygen ion conductivity, a standard electrode provided in the interior of said solid electrolyte and which produces a known value of oxygen partial pressure, and a counter electrode provided on the exterior of said solid electrolyte which determines a reference potential, said solid electrolyte being coated with a substance that provides a constant value of the activity of an oxide of the impurity element M in molten iron; at least one of a second sensor comprising a solid electrolyte having oxygen ion conductivity and which measures the activity, $a_o$, of free oxygen; and a third sensor for measuring the content of carbon in the molten iron, said first, second and/or third sensors being assembled in the single probe.

EXPLANATION OF REFERENCES IN THE DRAWINGS

1 ... standard electrode, 2 ... solid electrolyte, 3 ... coating layer, 4 ... molten iron, 5 ... lead wire from standard electrode, 6 and 14 ... lead wires from molten iron, 7 ... potentiometer, 9 ... closed tube, 10 ... cement, 11 and 12 ... first sensor, 13 ... second sensor, 15 ... thermocouple, 16 ... third sensor, 17 ... sample chamber, 18 ... lead wire, 19 ... point of contact, 20 ... cap, 23 ... protecting tube, 24 ... connector

PREFERRED EMBODIMENT OF THE INVENTION

The coating layer on the solid electrolyte of which the first sensor is made consists of an oxide of the impurity element to be analyzed or a composite oxide thereof and a binder which is typically a metal fluoride. The coating layer may contain a substance that renders it in either molten or semi-molten state. The solid electrolyte and the standard electrode may be of any type that is commonly employed in conventional oxygen sensors.

The impurity element that can be measured with the probe of the present invention is typically Al, Si, Mn, Ti, P, Mg, Cr, Ni or Cu. The substance that provides a constant value of the activity of an oxide of this impurity element is an oxide of the same. Therefore, if one of the elements listed above is to be measured, the substance that provides a constant value of the activity of that element is its respective oxide. e.g. $Al_2O_3$, $SiO_2$, MnO, $TiO_2$, $P_2O_5$, MgO, $Cr_2O_3$, NiO and CuO.

The substance that renders the coating layer in either molten or semi-molten state is for example, $CaF_2$, $MgF_2$, NaF or glass powder.

Figure 1:
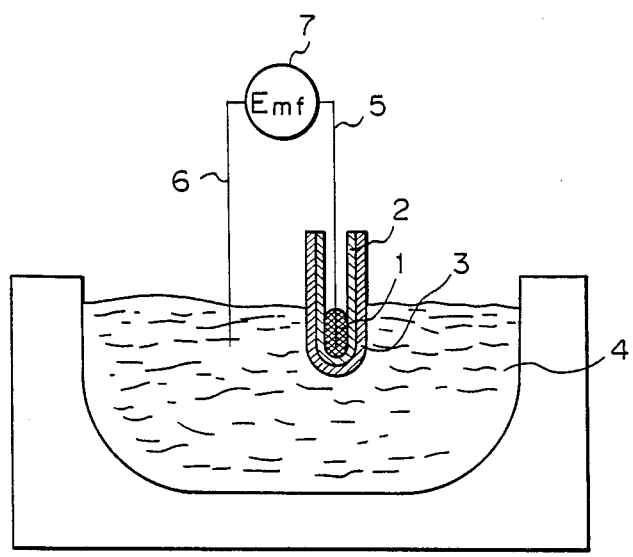
FIG. 1 and FIG. 2 schematically show the state in which the present probe is immersed in a molten iron.

FIG. 1 is a schematic diagram showing the first sensor of the present invention immersed in a molten metal. FIG. 1 is intended to illustrate the operating principle of the present invention, not the probe per se. In this figure, 1 is a standard electrode, 2 is a solid electrolyte, 3 is a coating layer, 4 is molten iron, 5 is a lead to the standard electrode, 6 is a lead to the molten iron, and 7 is a potentiometer.

Figure 2:
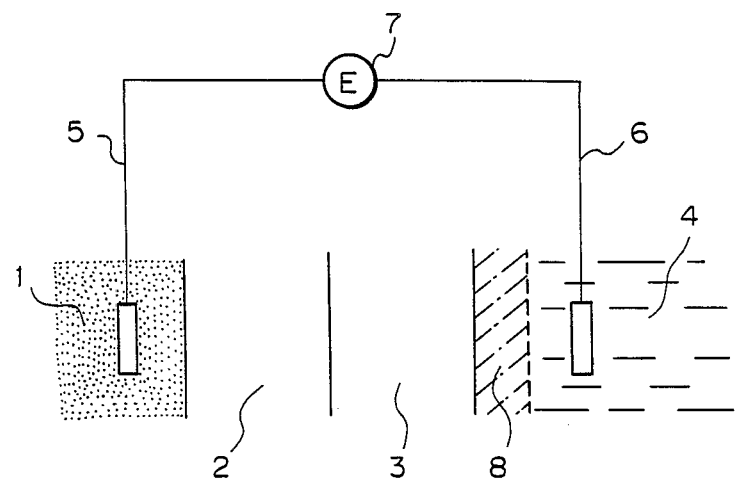
Figure 3:
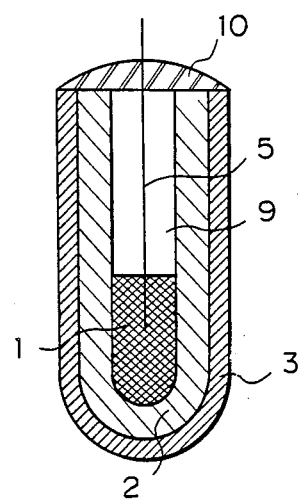
FIG. 3 is a sectional view showing the first sensor for measuring the concentration of the impurity element.

FIG. 2 shows graphically the theory of measurement with the first sensor of the present invention. In FIGS. 1 and 2, the like numerals identify like parts.

When, as shown in FIGS. 1 and 2, the coating layer that provides a constant value of the activity of an oxide of the impurity element to be measured in molten iron is present in the molten iron, the following reaction of equilibrium will be established in the vicinity of that coating layer:

$$M + \frac{x}{2} O_2 = MOx \quad (1)$$

where M stands for the impurity element to be measured, and O is oxygen. For the sake of clarity, the region in which the reaction represented by Equation (1) occurs is shown diagrammatically by 8 in FIG. 2.

In practice, the activity of $MO_x (a_{MOx})$, is unity or smaller than unity. A constant value of $a_{MOx}$ suffices for the purposes of the present invention. For the sake of convenience in the discussion that follows, the value of $a_{MOx}$ is dealt with as being unity. The equilibrium constant, $K_M$, of Equation (1) is expressed by:

$$KM = \frac{a_{MOx}}{a_M \cdot P_{O_2}^{\frac{x}{2}}} = \frac{1}{a_M \cdot P_{O_2}^{\frac{x}{2}}} \quad (2)$$

where $a_M$ signifies the activity of the impurity element of interest M; $PO_2$ is the oxygen partial pressure taking part in the reaction represented by Equation (1). Since KM depends solely upon temperature, $a_M$ can be obtained by measuring the temperature of the molten iron and $PO_2$, the latter being measured with an oxygen sensor. The electromotive force, E, of the oxygen sensor (i.e., the reading of the potentionmeter 7 in FIG. 1) is generally expressed by:

$$E = \frac{RT}{F} \ln \frac{P_{O_2}(II)^{\frac{1}{4}} + Pe'^{\frac{1}{4}}}{P_{O_2}(I)^{\frac{1}{4}} + Pe'^{\frac{1}{4}}} \quad (3)$$

where T is the temperature, F is Faraday's constant, R is a gas constant, $P_{O_2}(I)$ is the oxygen partial pressure at the standard electrode, Pe' is a parameter for partial electron conductivity, and $P_{O_2}(II)$ corresponds to $P_{O_2}$ in Equation (2) and is expressed by:

$$P_{O_2}(II) = \frac{1}{K_M \cdot a_M} \quad (4)$$

Substituting Equation (4) into Equation (3), we obtain:

$$E = \frac{RT}{F} \ln \frac{(K_M \cdot a_M)^{-\frac{1}{4}} + Pe'^{\frac{1}{4}}}{P_{O_2}(I)^{\frac{1}{4}} + Pe'^{\frac{1}{4}}} \quad (5)$$

Solving Equation (5) for $a_M$, we get:

$$a_M = \frac{\left(\left\{(P_{O_2}(I)^{\frac{1}{4}} + Pe'^{\frac{1}{4}}) \times \exp\frac{FE}{RT}\right\} - Pe'^{\frac{1}{4}}\right)^{-4}}{K_M} \quad (6)$$

By these procedures, the activity of a particularly impurity element in molten iron can be determined.

The relationship between the concentration of a solute component in molten iron and its activity is generally expressed by:

$$\log a_M = \log [\%N_M] + e_M[\%j] \quad (7)$$

wherein $[\%N_M]$ is the concentration of an impurity element as an object of measurement; $[\%j]$ is the concentration of other dissolved components; and $e_M$ is the interaction auxialiary coefficient. Accordingly, $[\%N_M]$ can be calculated from the equation (7) numerically.

The second item of the right side in Equation (7) should be noted "j" represents O, Ti, etc. which are present as impurities. Therefore, if the amounts of each of O, Ti, etc. are known, an accurate figure for $a_M$ can be figured out.

The present probe has at least one sensor that is able to measure one or more of the impurities.

The present probe has at least one first sensor, as well as a second sensor and/or a third sensor.

When one or more sensors which can measure the item of "j" simultaneously are used in the probe, the measuring accuracy can be increased.

The first sensor comprises a solid electrolyte having oxygen ion conductivity, a standard electrode provided in the interior of said solid electrolyte and which produces a known value of oxygen partial pressure, and a counter electrode provided on the exterior of said solid electrolyte and which determines a reference potential, said solid electrolyte being coated with a substance that provides a constant value of the activity of an oxide of the impurity element M in molten iron thereby determining activity $a_j$ of impurity element $M_j$ in the molten iron.

The second sensor comprises a solid electrolyte having oxygen ion conductivity and which measures the activity, $a_o$, of free oxygen from the partial pressure of oxygen.

The third sensor measures the content of carbon in the molten iron by utilizing depression of the freezing point.

A standard electrode is shown at 1. A solid electrode is shown at 2, a lead at 5 and a refractory cement cap at 10. Coating layer 3 is formed on the surface of solid electrolyte 2. Quartz or $Al_2O_3$ 9 is charged in the space of the standard electrode. Coating layer 3 contains a substance that makes the value of the activity of an oxide of the impurity element M in molten iron substantially constant.

Exemplary solid electrolytes contain $ZrO_2$-$MgO$ and $ZrO_2$-$Y_2O_3$, etc. Such solid electrolytes are well known.

When the impurity element to be measured is Si, the coating layer comprises 5–30 wt% of $CaF_2$ and 95–70 wt% of $SiO_2$. When the impurity element to be measured is Ti, the coating layer 3 comprises 5–30 wt% of $CaF_2$ and 95–70 wt% of $TiO_2$. After the mixture of $CaF_2$ and $SiO_2$ or the mixture of $CaF_2$ and $TiO_2$ is mixed with an organic binder, it is blended in a ball mill. Thereafter, the resulting coating material is coated on the solid electrolyte and dried.

The structures of the second sensor and the third sensor are well known.

Figure 4:
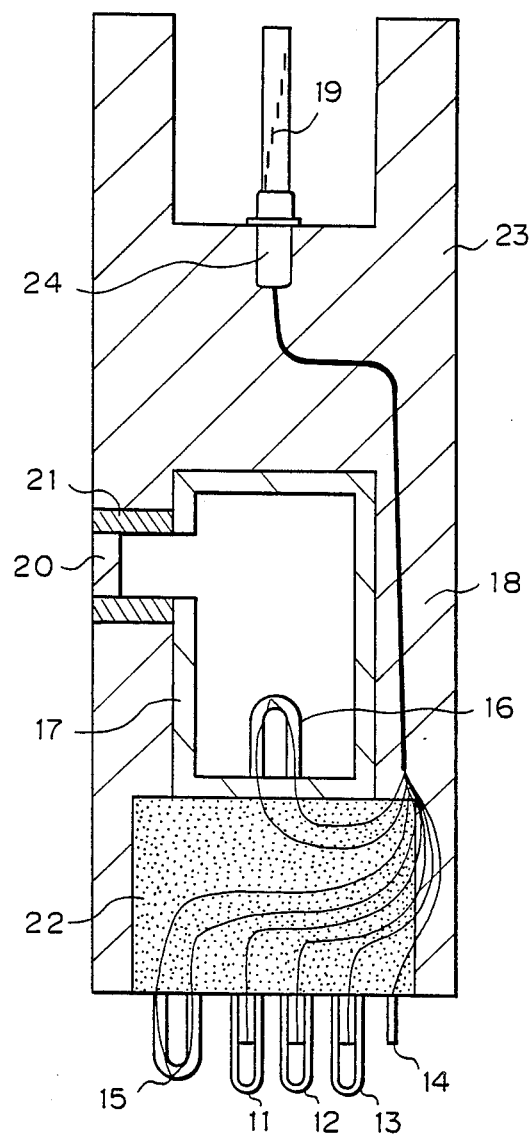
FIG. 4 is a sectional view showing the present composite probe.

FIG. 4 shows the present probe. The first sensors are shown at 11 and 12. The second sensor is shown at 13. The iron pole to be melted is shown at 14. A thermo couple is shown at 15.

Sensors 11, 12 and 13 and thermo couple 15 are assembled in the probe using refractory cement 22. A thermo couple for measuring the amount of carbon is shown at 16. A sample chamber for measuring the amount of carbon is shown at 17. The surface of sample chamber 17 is formed of iron or ceramics. Sample chamber 17 is preferably in a cylindrical form. Before the probe is used, sample chamber 17 may have a cap 20 formed of iron or paper. The inlet for molten iron is shown at 21. The freezing point of the molten iron is measured by a thermo couple 16. The amount of carbon contained in the molten iron can be calculated from the depression of the freezing point. The probe may be fitted into a protective tube 23 formed of paper or ceramic fibers. A lead wire is shown at 18 and a connector is shown at 24.

EXAMPLE

A composite probe capable of measuring the amounts Si, F, O and C simultaneously was used. The solid electrolytes constituting three kinds of sensors comprise $ZrO_2$ containing 8 mol % of $MgO$. The solid electrolyte of sensor 11 was coated with a material comprising 90 wt% of $SiO_2$, 10 wt% of $CaF_2$ and an organic binder in order to measure the concentration of Si in the molten iron. The solid electrolyte of sensor 12 was coated with a material comprising 90 wt% of $P_2O_5$, 10 wt% of $CaF_2$ and an organic binder in order to measure P. The solid electrolyte of sensor 13 for measuring the concentration of O was not coated with any material. The temperature of the molten iron was measured by using a thermo couple comprising Pt-PtRh (13%). The wire of the thermocoupled was protected with a U-tube (outer diameter, 3 mm and thickness, 1.0 mm) formed of silica glass. Thermocouple 16 was also protected by the same U-tube. Cement 22 was $Al_2O_2$ type cement.

The inner surface of the sample chamber was formed of iron. The sample chamber was in a cylindrical form having an inner diameter of 20 mm, an outer diameter of 40 mm and a length of 60 mm. Cap 20 and protecting tube 23 were formed of paper.

The probes as prepared above were immersed for 20 seconds into two kinds of molten irons, the amounts of carbon and oxygen of which are different from each other. The measuring conditions and the analysis values are shown in Table 1.

TABLE 1

|  | Temp. | Si % | C % | P % | activity of O |
|---|---|---|---|---|---|
| Condition A | 1480° | 0.15–0.05 | 3.00 | 0.01–0.08 | 10 |
| Condition B | 1490° | 0.15–0.05 | 4.75 | 0.01–0.08 | 3 |

Under the conditions specified above, the Si and P concentrations were measured using the composite probe of the present invention and two prior art Si and P activity sensors. The results of this comparative experiment are shown in FIGS. 5 and 6.

Figure 5:
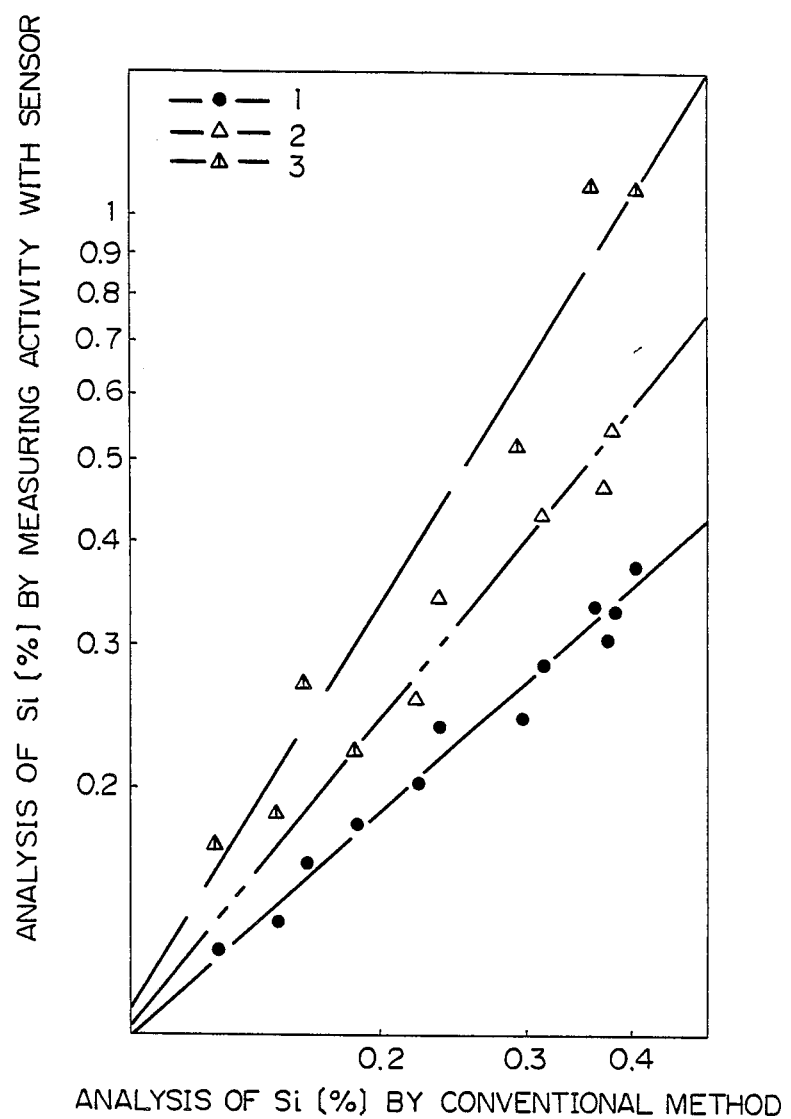
FIG. 5 is a graph showing the relationship between analysis of Si by using the present probe and conventional chemical analysis of Si.

FIG. 5 shows graphically the data for the measurements of Si concentration. Curve 1 shows the results obtained with the composite probe which correlated well to the analytical values in terms of fidelity and precision irrespective of whether the measurement was conducted under condition A or B. Curve 2 shows the results obtained with the Si activity sensor under condition A, whereas curve 3 shows the results obtained with the same sensor under condition B. The mismatch from the analytical data differed so greatly under the two conditions, the Si activity sensor was found to be unsuitable for use in practical applications.

Figure 6:
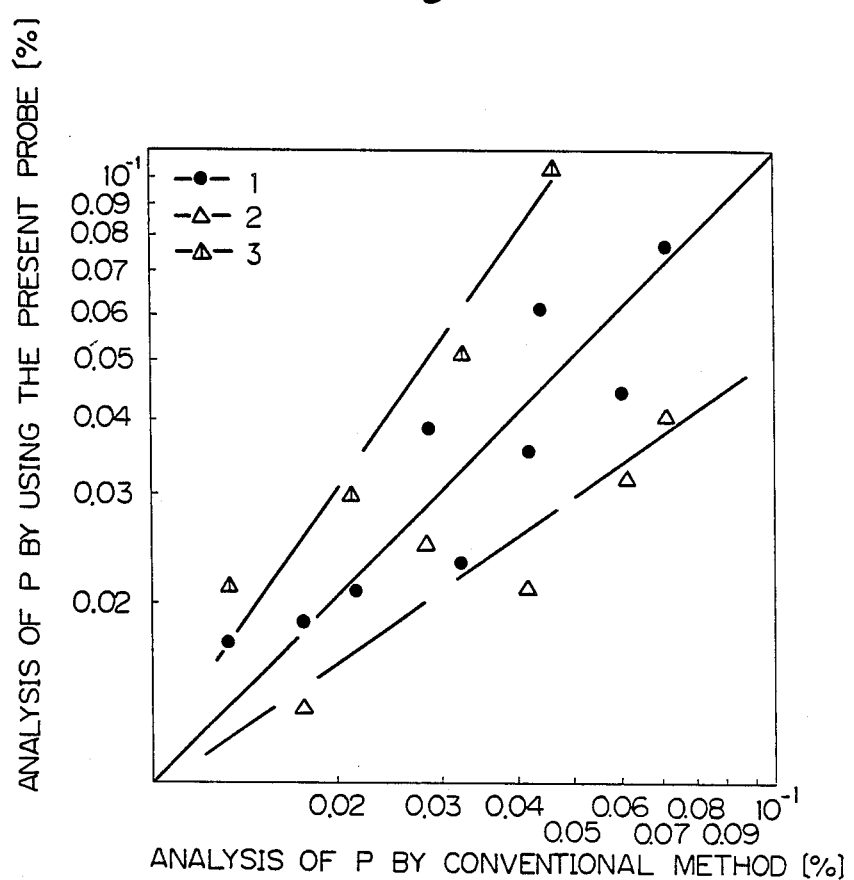
FIG. 6 is a graph showing the relationship between analysis of P by using the present probe and conventional chemical analysis of P.

FIG. 6 shows graphically the data for the measurements of P concentration. As in the case of Si measurement, curve 1 shows the results obtained with the composite probe which correlated well to the analytical values. However, as indicated curves 2 and 3, the P activity sensor was unable to produce reliable results under different conditions.

What is claimed is:

1. A composite probe for directly measuring the concentration of an impurity element in molten iron, said probe comprising:

(a) at least one first sensor for measuring the activity of an impurity element in molten iron, said first sensor comprising a solid electrolyte having oxygen ion conductivity, a standard electrode provided in the interior of said solid electrolyte and which produces a known value of oxygen partial pressure, and a counter electrode provided on the exterior of said solid electrolyte and which determines a reference potential, said solid electrolyte being coated with a substance that makes the value of the activity of an oxide of said impurity element in molten iron substantially constant; and (b) a second sensor comprising a solid electrolyte having oxygen ion conductivity which measures the activity of free oxygen; and (c) a third sensor for measuring the carbon content of the molten iron.

* * * * *